(12) United States Patent
McCarthy et al.

(10) Patent No.: US 7,492,980 B2
(45) Date of Patent: Feb. 17, 2009

(54) METHODS OF MAKING AND OPERATING A FIBER OPTIC SENSING DEVICE

(75) Inventors: Kevin Thomas McCarthy, Troy, NY (US); Kung-Li Justin Deng, Waterford, NY (US); Hua Xia, Altamont, NY (US); Michael Joseph Krok, Clifton Park, NY (US); Avinash Vinayak Taware, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 12/107,340

(22) Filed: Apr. 22, 2008

(65) Prior Publication Data
US 2008/0219618 A1   Sep. 11, 2008

Related U.S. Application Data

(62) Division of application No. 11/086,055, filed on Mar. 22, 2005, now Pat. No. 7,421,162.

(51) Int. Cl.
*G02B 6/34* (2006.01)
*G02B 6/26* (2006.01)

(52) U.S. Cl. .............................. 385/12; 385/13; 385/37

(58) Field of Classification Search ........................ None
See application file for complete search history.

(56) References Cited

U.S. PATENT DOCUMENTS

| | | | |
|---|---|---|---|
| 6,587,188 B2 | 7/2003 | Gleine et al. | |
| 6,591,038 B1 | 7/2003 | Pezeshki | |
| 6,640,020 B2 * | 10/2003 | Ionov | 385/10 |
| 6,766,080 B2 | 7/2004 | Ohmura et al. | |
| 6,999,659 B1 | 2/2006 | Nowak et al. | |
| 7,053,740 B1 | 5/2006 | Lascars et al. | |
| 7,127,132 B1 | 10/2006 | Moslehi et al. | |
| 2003/0035626 A1 | 2/2003 | Smith | |
| 2003/0152323 A1 | 8/2003 | Wakabayashi et al. | |
| 2004/0179797 A1 | 9/2004 | Po et al. | |
| 2006/0056959 A1 | 3/2006 | Sabol et al. | |

FOREIGN PATENT DOCUMENTS

GB   2245709   3/2003

* cited by examiner

*Primary Examiner*—Tina M Wong
(74) *Attorney, Agent, or Firm*—Ann M. Agosti

(57) ABSTRACT

In accordance with one exemplary embodiment the invention provides a multi-parameter fiber optic sensing system with an aperiodic sapphire fiber grating as sensing element for simultaneous temperature, strain, $NO_x$, CO, $O_2$ and $H_2$ gas detection. The exemplary sensing system includes an aperiodic fiber grating with an alternative refractive index modulation for such multi-function sensing and determination. Fabrication of such quasiperiodic grating structures can be made with point-by-point UV laser inscribing, diamond saw micromachining, and phase mask-based coating and chemical etching methods. In the exemplary embodiment, simultaneous detections on multi-parameter can be distributed, but not limited, in gas/steam turbine exhaust, in combustion and compressor, and in coal fired boilers etc. Advantageously, the mapping of multiple parameters such as temperature, strain, and gas using sapphire aperiodic gratings improves control and optimization of such systems directed to improve efficiency and output and reduce emissions.

20 Claims, 9 Drawing Sheets

METHODS OF MAKING AND OPERATING A FIBER OPTIC SENSING DEVICE

CROSS REFERENCE TO RELATED APPLICATIONS

This application is a division of U.S. patent application Ser. No. 11/086,055 entitled "FIBER OPTIC SENSING DEVICE AND METHOD OF MAKING AND OPERATING THE SAME" filed Mar. 22, 2005, now U.S. Pat. No. 7,421,162 which is herein incorporated by reference for all purposes.

BACKGROUND

The present invention relates generally to fiber optic sensing devices, and more particularly, to a fiber optic sensing device for detecting multiple parameters in an environment or element, for example. Indeed, the present invention provides advantages related to the use of fiber optic sensing devices in harsh environments, for instance.

Various sensing devices are known and are generally in use. For example, thermocouples are used for measuring the temperature in components of a device, such as exhaust systems, combustors, compressors and so forth. Yet other sensing systems are employed to detect physical parameters such as, strain or temperature in an infrastructure. As one example, Bragg grating sensors are often employed. However, such conventional sensing devices are limited by the operational conditions in which they may be employed. For example, conventional sensing devices are often limited to relatively mild temperature conditions and, as such, limited operational temperature ranges. Indeed, conventional devices are limited to temperatures between +80° C. to +250° C., depending upon the fiber grating coating materials.

As such, it is difficult to measure temperatures for components in high-temperature environments like turbines and engines. Further, for large components, a relatively large number of discrete thermocouples may be required to map the temperatures. Such discrete thermocouples may not be scalable to meet a desired spatial resolution that is generally beneficial for accurate thermal mapping of system components, which can then used to control and optimize the operation of such systems with the objectives of improving efficiency and output. A more accurate and improved spatial resolution thermal mapping is necessary to control such systems (gas turbines, steam turbines, coal-fired boilers, etc.) with more accuracy and fidelity to meet requirements such as better efficiency and output. The sensing devices for gas components such as NOx, CO and O2 also have a similar limitation in terms of accuracy and spatial resolution. A more accurate and spatially dense gas sensing would facilitate more effective and efficient emissions control for gas turbines and coal-fired boilers.

Accordingly, conventional sensing devices present limitations when employed in high temperature and/or harsh environments such as, gas/steam turbine exhausts, coal-fired boilers, aircraft engines, downhole applications and so forth. For example, conventional Bragg grating sensors employ a doped or chemical grating that breaks down in high temperature settings (e.g., a gas turbine exhaust that may reach temperatures of 600° C. or higher).

Certain other conventional systems employ Bragg grating sensors for measuring and monitoring a parameter in an environment. Such sensors utilize a wavelength encoding within a core of the sensor to measure a parameter based upon a Bragg wavelength shift that is generated on illumination of the grating through an illumination source. Thus, environmental effects on the periodicity of the grating alters the wavelength of light reflected, thereby providing an indication of the environmental or elemental effect, such as, temperature or strain, for example. However, it is difficult to simultaneously detect multiple parameters, such as temperature and gas, through a single conventional Bragg grating sensing element. Further, multiple spectral signals at different wavelengths may be required to separate the effect of multiple sensed parameters from one another. Such separation of sensed parameters is conventionally a difficult and time-consuming process.

In certain conventional sensor systems, an additional grating element encapsulated in a different material is placed in series with an existing grating element for separating the effects of two different parameters, such as temperature and strain. Moreover, such systems require overwriting gratings at the same fiber location, which often present difficulties during the manufacturing the fiber grating for the sensor. In summary, conventional Bragg grating sensors do not facilitate discernment of what environmental or elemental factor influenced the sensor, rather only the physical changes in the sensor itself are readily detectable.

Therefore, there is a need for improved sensing devices.

BRIEF DESCRIPTION

In accordance with one exemplary embodiment, the present technique provides a fiber optic grating sensor cable. Each exemplary fiber grating includes a core having a first index of refraction and a plurality of grating elements each having an index of refraction different from the first index of refraction. The core includes a first pair of grating elements configured to reflect a first wavelength of light in phase and a second pair of grating elements configured to reflect a second wavelength of light in phase. The core also includes a third pair of grating elements configured to reflect the first wavelength of light in phase, wherein at least one grating element of the second pair of grating elements is located between at least one grating element of the first pair and at least one grating element of the third pair. The fiber optic sensor cable also includes a cladding disposed circumferentially about the core.

In accordance with yet another exemplary embodiment, the present technique provides a method of detecting a plurality of parameters. The method includes providing a source of light to a fiber optic sensor cable having a plurality of grating elements and comprising first, second and third portions, wherein adjacent gratings in the first and third portions are at a first distance from one another and adjacent gratings in the second portion are at a second distance from one another, and wherein the second portion is located between the first and third portions. The method also includes detecting light emitted from the fiber optic sensor cable.

In accordance with another exemplary embodiment, the present technique provides a distributed sensor system for sensing multiple parameters in a harsh environment. The sensor system includes a plurality of sensors disposed on a distributed fiber optic grating sensor cable, wherein each of the plurality of sensor comprises a core having a first index of refraction and a plurality of mechanically altered portions each having an index of refraction different than the first index of refraction.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
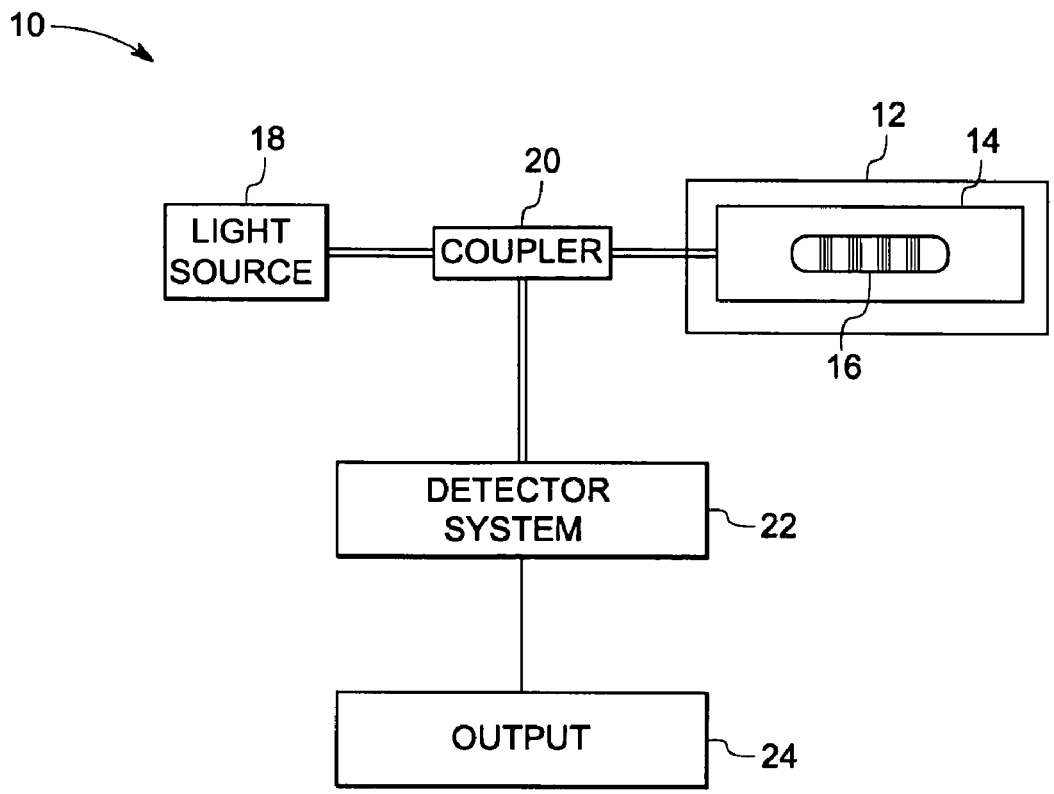
FIG. 1 is a diagrammatical representation of a fiber optic sensing system for detecting multiple parameters of an environment and/or element, in accordance with an exemplary embodiment of the present technique.

Referring now to drawings, FIG. 1 illustrates an exemplary fiber optic sensing system 10 for detecting parameters of an environment and/or object 12. Although the present discussion focuses on sensing devices and systems, the present technique is not limited to sensing field, but is also applicable to other modalities, such as, optical filters, data transmission, and telecommunications, among others. Accordingly, the appended claims should not be limited to or by the exemplary embodiments of the following discussion. The fiber optic sensing system 10 includes a fiber optic sensing device 14 that, in turn, includes a grated cable 16. As illustrated, the cable 16 is disposed within the element 12, causing changes in the element 12 to translate to the cable 16. The grated cable 16 includes a core that has a plurality of grating elements arranged in an aperiodic pattern, which is described in detail below. In the present discussion, a grating element refers to a variance in the index of refraction in comparison to the index of refraction of the core. Such grating elements may be a result of a micromachining process, such as diamond saw cutting, or a chemical process, such as doping, and both processes are discussed further below.

Further, the fiber optic sensing system 10 includes a light source 18 that is configured to illuminate the core of the grated cable 16. This illumination facilitates the generation of reflected signals corresponding to a grating period of the grated cable 16. The system 10 also includes an optical coupler 20 to manage incoming light from the light source 18 as well as the reflected signals from the grated cable 16. Indeed, the coupler 20 directs the appropriate reflected signals to a detector system 22.

The detector system 22 receives the reflected optical signals from the grated cable 16 and, in cooperation with various hardware and software components, analyzes the embedded information within the optical signals. For example, the detector system 22 is configured to estimate a condition or a parameter of the object 12 based upon a diffraction peak generated from the plurality of grating elements of the grated cable 16 of the fiber optic sensing device 14. In certain embodiments, the detector system 22 employs an optical coupler or an optical spectral analyzer to analyze signals from the fiber optic sensing device 14. Depending on a desired application, the detector system 22 may be configured to measure various parameters in the environment 12. Examples of such parameters include temperatures, presence of gases, strains and pressures, among others.

Advantageously, as discussed further below, the exemplary cable 16 generates multiple strong diffraction peaks, thereby facilitating the segregation of the various influencing parameters on the cable 16. The information developed by the detector system 22 may be communicated to an output 24 such as, a display or a wireless communication device. Advantageously, gleaned information, such as environmental or object conditions, may be employed to address any number of concerns or to effectuate changes in the environment or object 12 itself.

Figure 2:
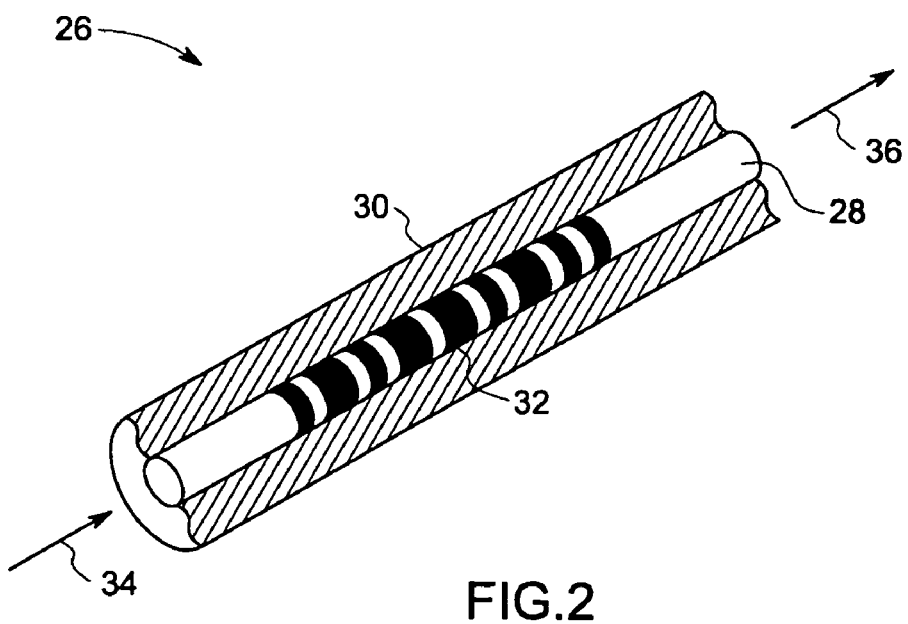
FIG. 2 is a diagrammatical representation of a fiber optic sensor array cable having aperiodic spaced grating structures with the refractive index modulated by a periodic or an aperiodic sequence, in accordance with an exemplary embodiment of the present technique.

FIG. 2 illustrates an exemplary fiber optic sensor array cable 26 having an aperiodic grated refractive index modulation, in accordance with an embodiment of the present technique. The fiber optic sensor cable 26 includes a core 28 and a cladding 30 that is disposed circumferentially about the core 28. A portion of the cladding 30 has been removed to better illustrate the underlying core 28. The core 28 includes a series of grated elements 32 that are configured to reflect in phase wavelengths of light corresponding to a grating period of the grated elements 32. As illustrated, distances between adjacent gratings are arranged in an aperiodic pattern that will be described in detail below with reference to FIG. 3. During operation, an input broadband light signal 34 is provided to the fiber optic sensor cable 26 by the light source 18 and a portion of the input broadband light signal 34 is reflected by a respective grating element 32 in phase and corresponding to certain wavelengths of light, while remaining wavelengths are transmitted as represented by a transmitted signal 36.

Figure 3:
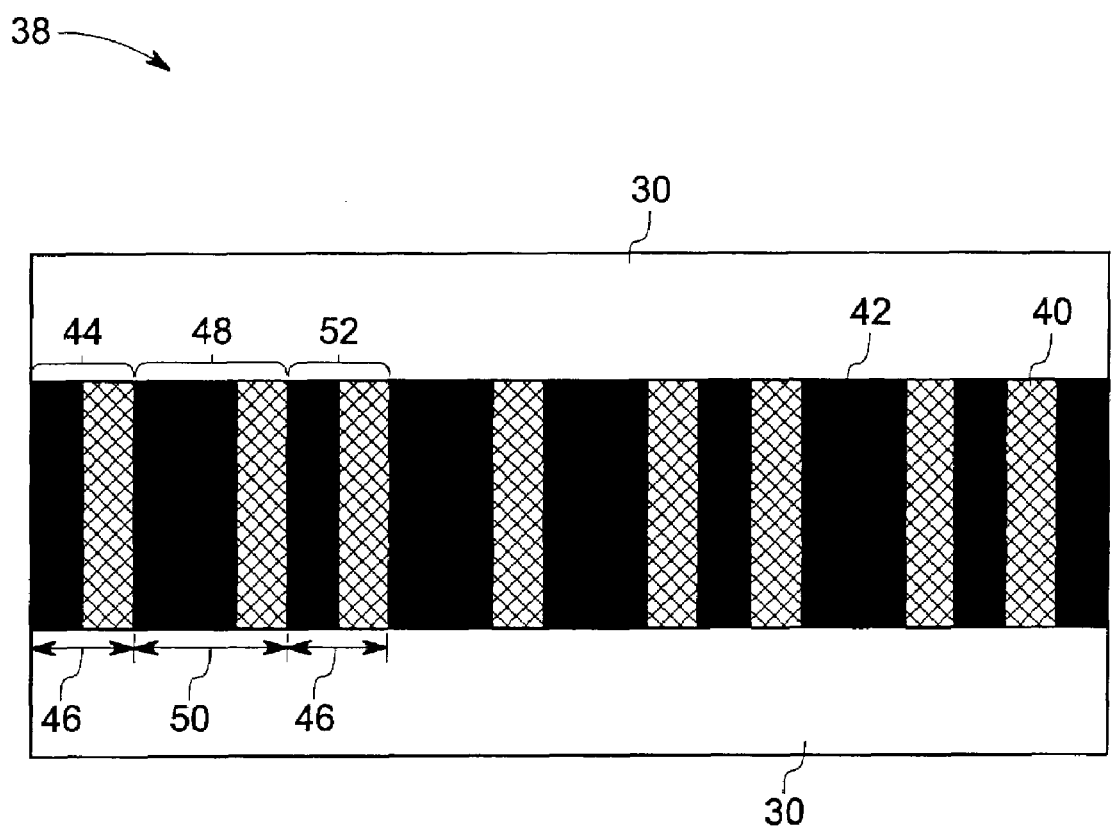
FIG. 3 is a diagrammatical representation of the core of a fiber optic sensor cable including aperiodic grating structures.

Referring now to FIG. 3, a grated portion of a core of a fiber optic sensor cable 38 is illustrated. As illustrated, the fiber optic sensor cable 38 is formed of a core 40 and cladding 30 that is disposed about the core 40. The cladding 30 provides for near total internal reflection of light within the cable 38, thereby allowing light to be transmitted by and axially through the cable 38. The cable 38 also includes a plurality of grating elements represented generally by reference numeral 42. In one embodiment, the core 40 comprises a fused silica fiber. In another embodiment, the core 40 comprises a sapphire fiber. The plurality of grating elements 42 has an index of refraction different from that of core 40. In this embodiment, the index of refraction of the grating elements 42 is lower than that of the core 40. By way of example, the core 40 may have an index of refraction of 1.48, while the grating element 42 may have an index of refraction of 1.47, for instance. As discussed below, the index of refraction of the various grating elements 42, and the distances between these grating elements 42 defines the wavelength of light reflected in phase by the grating elements 42.

The exemplary portion of the core 40 shown in FIG. 3 includes various portions that effect how light is transmitted through the fiber optic sensor cable 38. In the illustrated embodiment, the core 40 includes a first portion 44 where the distance between adjacent grating elements 42 is at a first distance 46. This first distance 46 defines a first wavelength of light that will be reflected in phase by the pair of grating elements 42 in the first portion 44. By way of example, the distance between the first pair of grating elements 42 is generally of the same order of magnitude as that of the wavelength of the reflected light, e.g., 0.775 µm, for instance. The core also includes a second portion 48 where the distance between adjacent grating elements 42 is at a second distance 50. This second distance 50, which is different than the first distance 46 defines a second different wavelength of light that will be reflected in phase by the pair of second grating elements 42 in the second portion 48. In addition, the core 40 includes a third portion 52 where the distance between grating elements 42 is at the first distance 46. Thus, the grating elements 42 in the third portion 52 reflect the first wavelength of light in phase, like the first portion 44. In this embodiment, the second portion 48 is disposed between the first and third portions 44 and 52.

As can be seen, the distances between adjacent gratings 42 have an aperiodic pattern. That is, the distances between adjacent gratings 42 along a longitudinal axis of the core 40 alternate between the first and second distance 46 and 50. It is worth noting that the present oscillation between the first and second distances 46 and 50 to establish an aperiodic pattern is merely but one example. Indeed, a number of aperiodic patterns may be envisaged. In the illustrated embodiment, the indices of refraction of the core 40 and the gratings 42 are modulated according to Fibonacci sequence. The indices of refraction of the core 40 and the gratings 42 are modulated such that there is a relatively higher refractive index modulation with aperiodic sequence in the core 40 as compared to the refractive index modulation circumferentially surrounding the cladding 30. Further, the grating structure of the fiber core 40 may be defined by an aperiodic sequence of blocks $n_a$ and $n_b$ and a constant τ. By way of example, $n_a$ is index of refraction of 1.49 and $n_b$ is an index of refraction of 1.45.

In this embodiment, the sequence for the refractive index modulation is based upon the following equation:

$$S_3 = \{S_2, S_1\}, \ldots S_n = \{S_{j-1}, S_{j-2}\} \text{ for } j \geq 2 \quad (1)$$

where $S_1 = n_a$ corresponding to core region having the first effective index of refraction; and $S2 = n_a n_b$ corresponding to grating elements having an index of refraction different than the first index of refraction.

Thus, the diffraction spectrum generated by the above defined grating structure will include a first Bragg diffraction peak that corresponds to the first wavelength of light in phase and a second Bragg diffraction peak that corresponds to the second wavelength of reflected light in phase and a plurality of diffraction peaks that are determined by a modulation periodicity and a diffraction wave vector. In this exemplary embodiment, the modulation periodicity is based upon the following equation:

$$\Lambda = d(n_A) + \tau d(n_B) \quad (2)$$

where $d(n_A)$ and $d(n_B)$ are fiber lengths of the refractive index changed and unchanged areas respectively with τ being the golden mean with a value of 1.618.

Further, the diffraction wave vector is determined by two indices (n,m):

$$k(n,m) = (m + \tau n)/\Lambda \quad (3)$$

where Λ is a quasiperiodicity of the aperiodic grating structure and n, m are discrete wave numbers.

In the illustrated exemplary embodiment, the diffraction of light may occur when the discrete wave numbers satisfy the range n,m=0, ±1, ±2 . . . .

Further, the Bragg diffraction wavelength having relatively high intensity is given by:

$$\lambda_B(n, m) = \frac{2n_{eff}\Lambda}{(m + n\tau)}$$

Advantageously, a plurality of generated diffraction peaks facilitate simultaneous multiple parameters measurements. Examples of such parameters include temperature, strain, pressure and gas.

The illustrated aperiodic pattern of the gratings 42 of the fiber optic sensing device 38 enables the fiber optic sensing device 38 to generate a plurality of diffraction peaks simultaneously from emitted light from the core 40. In this exemplary embodiment, the plurality of diffraction peaks is representative of a plurality of sensed parameters such as, temperature, strain and so forth. The grated cable of the fiber optic sensing device 38 is configured to generate first and second diffraction peaks that contain embedded information representative of first and second sensed parameters. Such first and second diffraction peaks are then detected by the detector system 22 (see FIG. 1) for estimating the first and second sensed parameters. Advantageously, the grated cable allows the fiber optic sensing device 38 to generate the first and second diffraction peaks to appear in fiber low-loss transmission windows and also with substantially comparable efficiencies. The first and second diffraction peaks may be employed for simultaneously measuring the first and second sensed parameters such as temperature and strain. These first and second diffraction peaks corresponding to first and second sensed parameters are described below with reference to FIG. 4.

Figure 4:
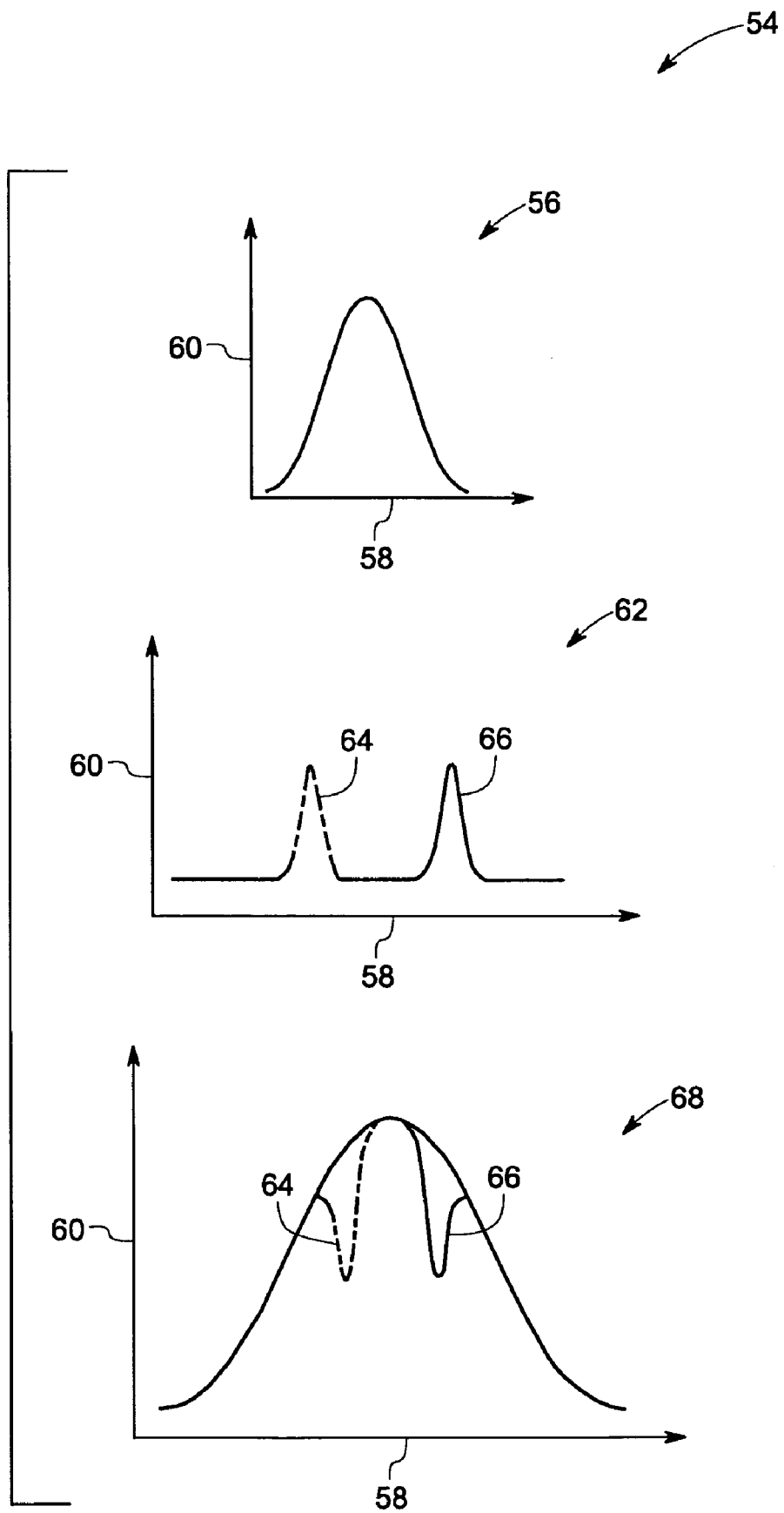
FIG. 4 is a diagrammatical representation of waveforms of light generated by aperiodic grating structures of the fiber optic sensor cable of FIG. 3, in accordance with an exemplary embodiment of the present technique.

FIG. 4 illustrates exemplary waveforms 54 of light generated by the aperiodic grated cable of the fiber optic sensing device of FIG. 3. The abscissa axis 58 of the waveforms 54 represents a wavelength of the light signal and the ordinate axis 60 of the waveforms 54 represents an intensity of the light signal. In the illustrated embodiment, an input broadband light signal is represented by a waveform 56 and a reflected signal from the grated cable is represented by reference numeral 62. As can be seen, the reflected signal 62 from the core of the grated cable includes first and second diffraction peaks 64 and 66 that may be processed by the detector system 22 (see FIG. 1) to estimate the first and second sensed parameters. Further, the transmitted signal is represented by a reference numeral 68 that transmits wavelengths that are not corresponding to the grating period of the grated cable 32. Thus, the aperiodic grated structure facilitates the generation of strong first and second diffraction peaks 64 and 66 with comparable diffraction efficiencies that can be detected by a single detector. These detected diffraction peaks 64 and 66 may then be processed to detect multiple parameters of the environment or object 12 (see FIG. 1). Advantageously, these diffraction peaks 64 and 66 can be maintained over relatively long lengths of cable without signal deterioration due to losses.

Figure 5:
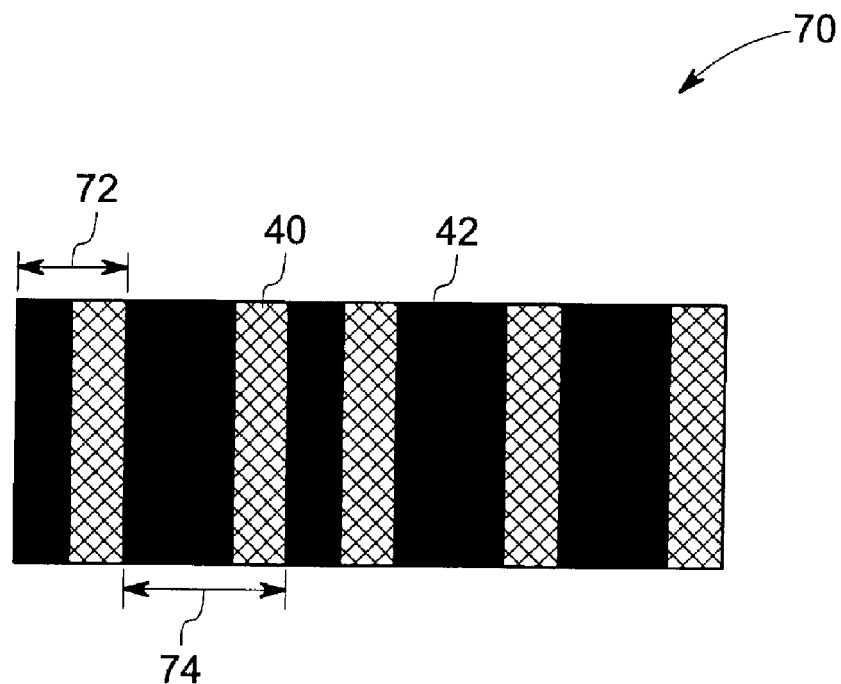
FIG. 5 is a diagrammatical representation of a Bragg grating fiber optic cable of FIG. 3 during normal conditions, in accordance with an exemplary embodiment of the present technique.

Referring now to FIG. 5, the Bragg grating fiber optic sensor cable 70 of FIG. 3 during normal conditions is illustrated. In the illustrated embodiment, the distance between a first pair of grating elements 42 is at a first distance 72 and the distance between a second pair of grating elements 42 is at a second distance 74. As described earlier, the illustrated aperiodic pattern of the distance between adjacent grating elements enables generation of two diffraction peaks from the fiber optic sensor cable 70 that are representative of two sensed parameters. In operation, when the fiber optic sensing device 70 is subjected to a stress for example, a temperature, or a strain, the distance between the adjacent grating elements changes in response to the applied stress as can be seen in FIG. 6.

Figure 6:
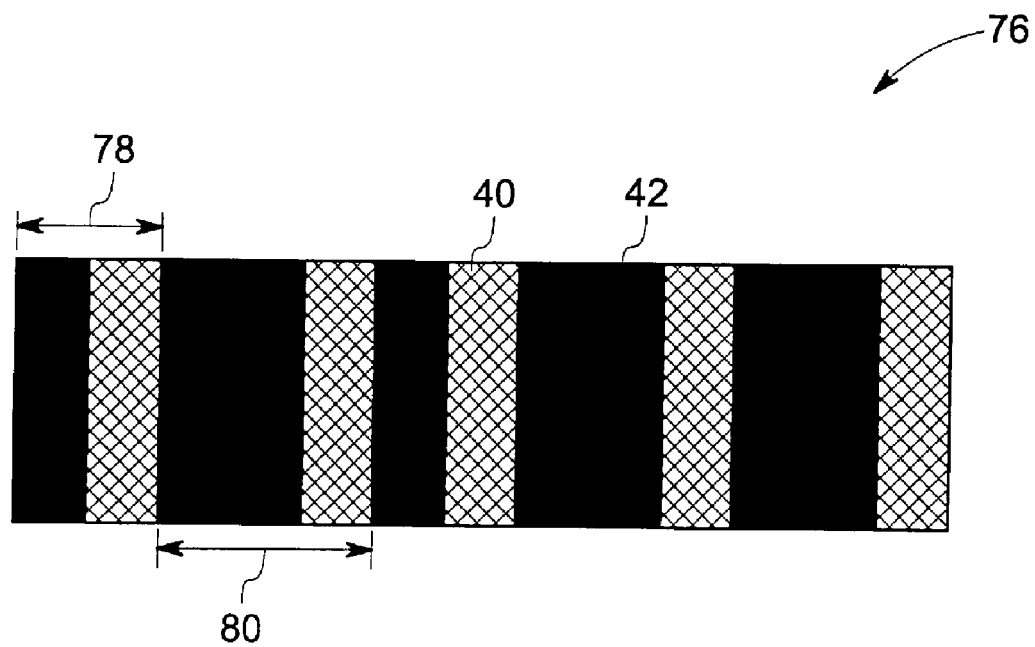
FIG. 6 is a diagrammatical representation of a Bragg grating fiber optic cable of FIG. 3 during stressed conditions, in accordance with an exemplary embodiment of the present technique.

FIG. 6 illustrates an exemplary Bragg grating fiber optic sensor cable 76 of FIG. 3 during stressed conditions. In this embodiment, the length of the fiber optic sensor cable 76 changes in response to an environmental condition, such as an applied stress and temperature. Therefore, the distance between the first pair of elements 42 changes from the first distance 72 (shown in FIG. 5) to a new distance 78, and this new distance 78 may be greater or lesser than the original distance 72. Similarly, the distance between the second pair of elements 42 changes from the second distance 74 (shown in FIG. 5) to a new distance 80. Again, this new distance 80 may be greater or lower than the second distance 74 depending on the influence of the environmental factors on the cable 76. On illumination of the fiber optic sensing device 76 through an illumination source, diffraction peaks are generated from the light emitted from the fiber optic sensing device 76. These diffraction peaks correlate to a change in length of fiber optic sensing device such as represented by the change in first and second distances 78 and 80 to estimate parameters corresponding to the diffraction peaks.

Similarly, in a gaseous environment, gases may interact with the fiber cladding, causing a change in the index of refraction resulting in cladding modes wavelength shifts that may be detected by the fiber optic sensing device 76 to simultaneously distinguish the temperature and gas effects. In this embodiment, the gases in the environment are detected from the optical properties variation of a sensing film that is coated on the grating elements of the fiber optic sensing device 76. The absorption and adsorption properties of a gas varies the cladding absorption properties and thereby the index of refraction. Thus, the reflectance and transmittance spectra associated with the light through the grating of the sensing device 76 enables the separation of the environmental effects of the temperature and strain from gas sensing. That is to say, the effects of the environment change the wavelengths of light reflected in phase by the cable 76. Further, by comparing this change with the diffraction peaks of the cable in its quiescent state, the magnitude of the environment effects can be determined.

Figure 7:
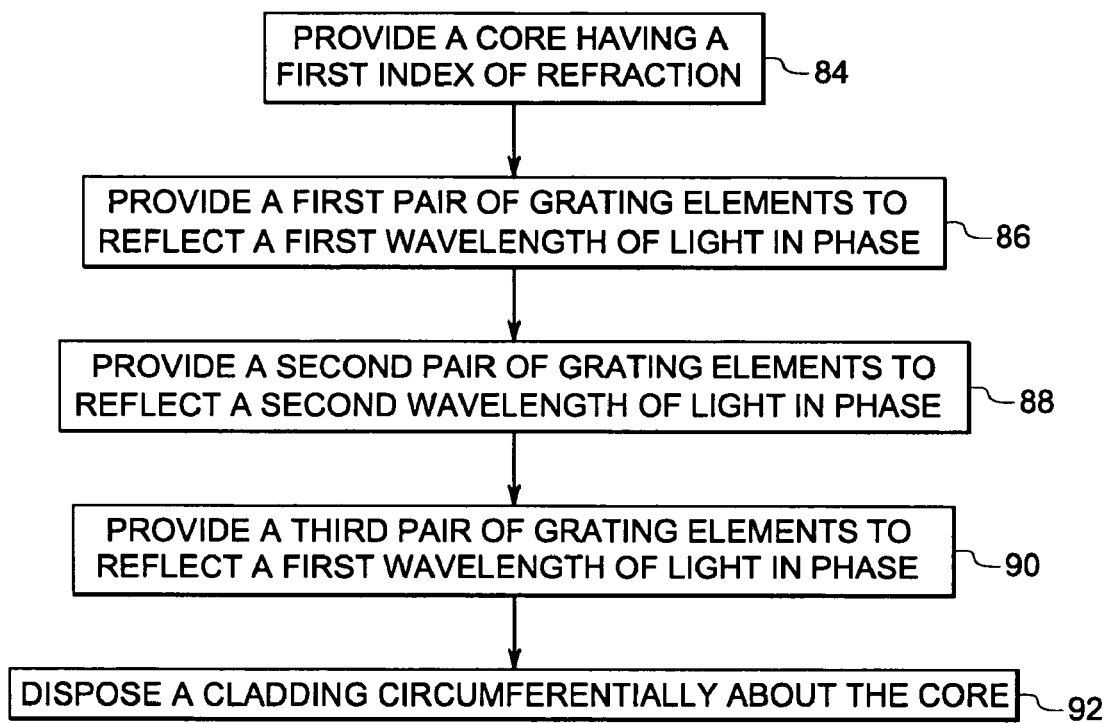
FIG. 7 is a flow chart of a process for manufacturing the fiber optic sensor cable of FIGS. 1-3, in accordance with an exemplary embodiment of the present technique.

The fiber optic sensing device of FIGS. 1-3 may be manufactured by an exemplary process as represented by reference numeral 82 in FIG. 7. The process 82 begins at step 84 where a core is provided. In this embodiment, the core has a first index of refraction. At step 86, a first pair of grating elements is provided wherein the distance between adjacent grating elements of the first pair is at a first distance. In the illustrated embodiment, the first pair of grating elements is configured to reflect a first wavelength of light in phase. At step 88, a second pair of grating elements is provided that is configured to reflect a second wavelength of light in phase. The distance between adjacent grating elements of the second pair is at a second distance. In this embodiment, the second distance is different than the first distance. As represented by step 90, a third pair of grating elements that is configured to reflect the first wavelength of light in phase is provided. In this embodiment, at least one grating element of the second pair of grating elements is located between at least one grating element of the first pair and at least one grating element of the third pair. As illustrated by step 92, a cladding is disposed circumferentially about the core. In one embodiment, the first, second and third pair of grating elements are provided through an ultraviolet light exposure laser inscribing technique. In another embodiment, the first, second and third pair of grating elements are provided by disposing an optical coating on the core and subsequently selectively removing portions from the core along a longitudinal axis of the core. In certain embodiments, the optical coating on the core may be etched through a slit pattern mask to provide the first, second and third pair of grating elements.

Figure 8:
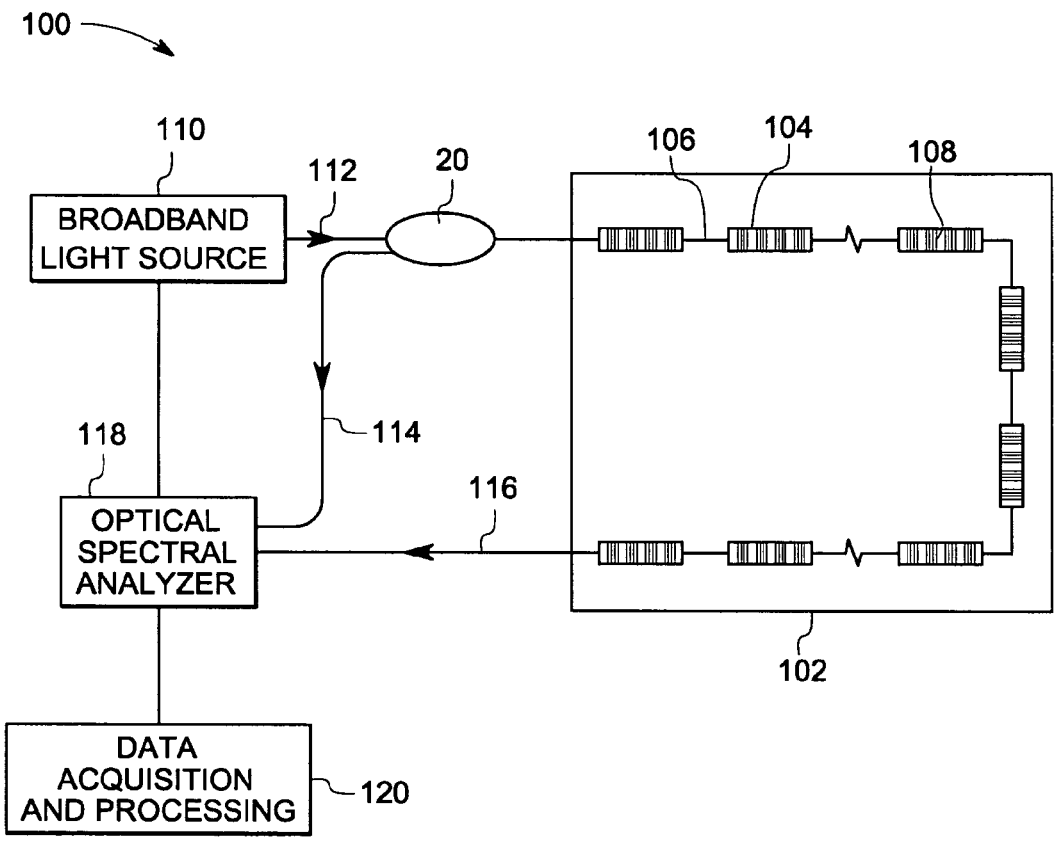
FIG. 8 is a diagrammatical representation of a distributed fiber sensor system, in accordance with an exemplary embodiment of the present technique.

The fiber optic sensing device manufactured by exemplary process of FIG. 7 may be employed for sensing parameters in a distributed environment. FIG. 8 illustrates an exemplary distributed fiber sensor system 100 for sensing parameters over a relatively large environment 102. In the illustrated embodiment, the sensor system 100 includes a plurality of sensors 104 disposed on a distributed cable 106. Further, each of the plurality of sensors 104 includes a grated cable 108. In certain embodiments, the grated cable 108 comprises a plurality of grating elements arranged in a periodic pattern. In certain other embodiments, the grating cable 108 comprises a plurality of grating elements arranged in an aperiodic pattern as described above. In the distributed sensor system 100, data regarding different locations of the environment can be obtained by evaluating the changes in the diffraction peaks reflected by the various sensors 104.

In operation, the distributed fiber sensor system 100 may be placed in the environment 102 for detecting parameters of environment such as temperature, strain and so forth. The distributed fiber sensor system 100 is illuminated by a light source 110 as represented by the reference numeral 112 and respective reflective and transmitive signals 114 and 116 are then received by an optical spectral analyzer 118. A coupler 20 may be coupled to the light source 110 and to the optical spectral analyzer 118 to combine the input and the reflected signal. The optical spectral analyzer 118 measures the wavelength spectrum and intensity of the received signals to estimate a parameter of the environment 102. Finally, the detected signals representative of the sensed parameters are transmitted to a data acquisition and processing circuitry 120.

Figure 9:
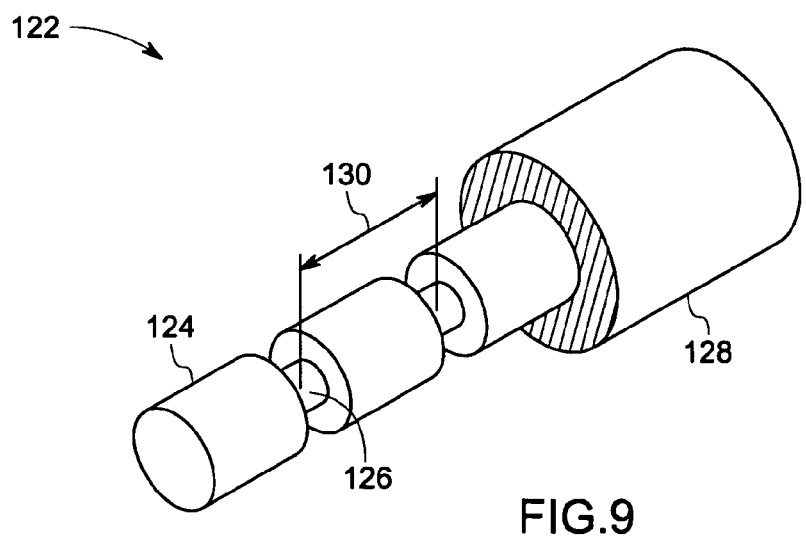
FIG. 9 is a diagrammatical representation of a fiber optic sensor cable with a micromachined aperiodic grating structure, in accordance with an exemplary embodiment of the present technique.

Referring now to FIG. 9, a fiber optic sensor cable 122 with a micro machined or mechanical structure is illustrated. The fiber optic sensor cable 122 includes a core 124 and a plurality of mechanically altered portions 126. Additionally, the fiber optic sensor cable 122 includes a cladding 128 disposed about the core 124 and the mechanically altered portions 126. In the illustrated embodiment, each of the mechanically altered portions comprises portions with diameter different than the diameter of the core. In certain embodiments, a micromachining process, such as diamond saw cutting process, may be employed for selectively removing portions of the core 124 to form the mechanically altered portions 126 by altering the diameter of the core 124. This micromachining process enables to create areas of refractive index that is different than the index of refraction of the core 124 and this variance in index of refraction functions as grating elements for the fiber optic sensor cable 122.

In certain exemplary embodiments, the distance between adjacent grating elements, such as represented by reference numeral 130, may vary along a longitudinal axis of the core 124 to form an aperiodic grating structure (as shown in FIG. 9). As described above with reference to FIG. 3, the aperiodic grating structure may be defined by an aperiodic sequence of blocks $n_a$ and $n_b$ and a constant $\tau$ and the sequence is based upon the following equation:

$$S_3=\{S_2,S_1\},\ldots S_n=\{S_{j-1},S_{j-2}\} \text{ for } j \geq 2 \quad (1)$$

where $S_1=n_a$ that corresponds to core region having the first index of refraction; and $S2=n_a n_b$ that corresponds to grating elements having an index of refraction different than the first index of refraction.

It should be noted that, the mechanically altered portions 126 of the grating structure manufactured by the micromachining processes enable the fiber optic sensor cable 122 to be employed in harsh environments such as a gas turbine exhaust, a steam turbine exhaust, a coal-fired boiler, an aircraft engine, a down hole application and so forth where the temperatures reach 600° C. and above, for instance.

Figure 10:
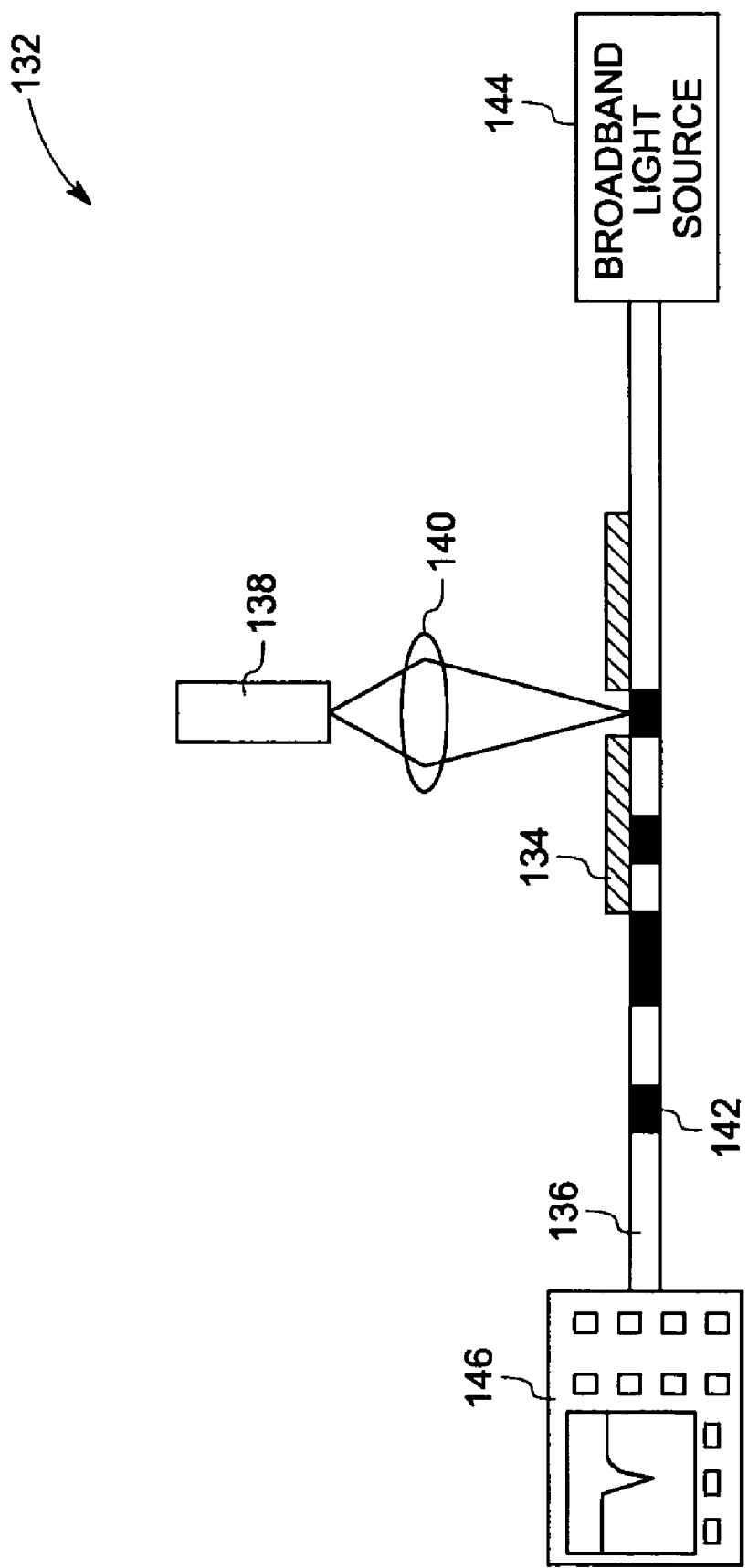
FIG. 10 is a diagrammatical representation of a system for inscribing the fiber grating structures of FIG. 3, in accordance with an exemplary embodiment of the present technique.

The aperiodic grating structure described above may also be formed by employing a point-by-point laser inscribing technique. Referring now to FIG. 10, a system 132 for inscribing Bragg grating is illustrated. The system 132 includes a phase mask 134 disposed on a fiber core 136. The system 132 also includes a UV laser 138 to generate a beam that is directed towards the phase mask 134. Further, the beam generated from the UV laser 138 may be focused with a plane cylindrical lens 140 towards the fiber core 136. In this embodiment, the phase mask 134 is employed to spatially modulate and diffract the UV beam from the UV laser 138 to form an interference pattern. The interference pattern induces a refractive index modulation that creates a Bragg grating structure 142 in the fiber core 136. The system 132 also includes a broadband light source 144 and an optical spectrum analyzer 146 for detecting the Bragg wavelength of the light wave that is received by the optical spectrum analyzer 146 from the fiber core 136.

Figure 11:
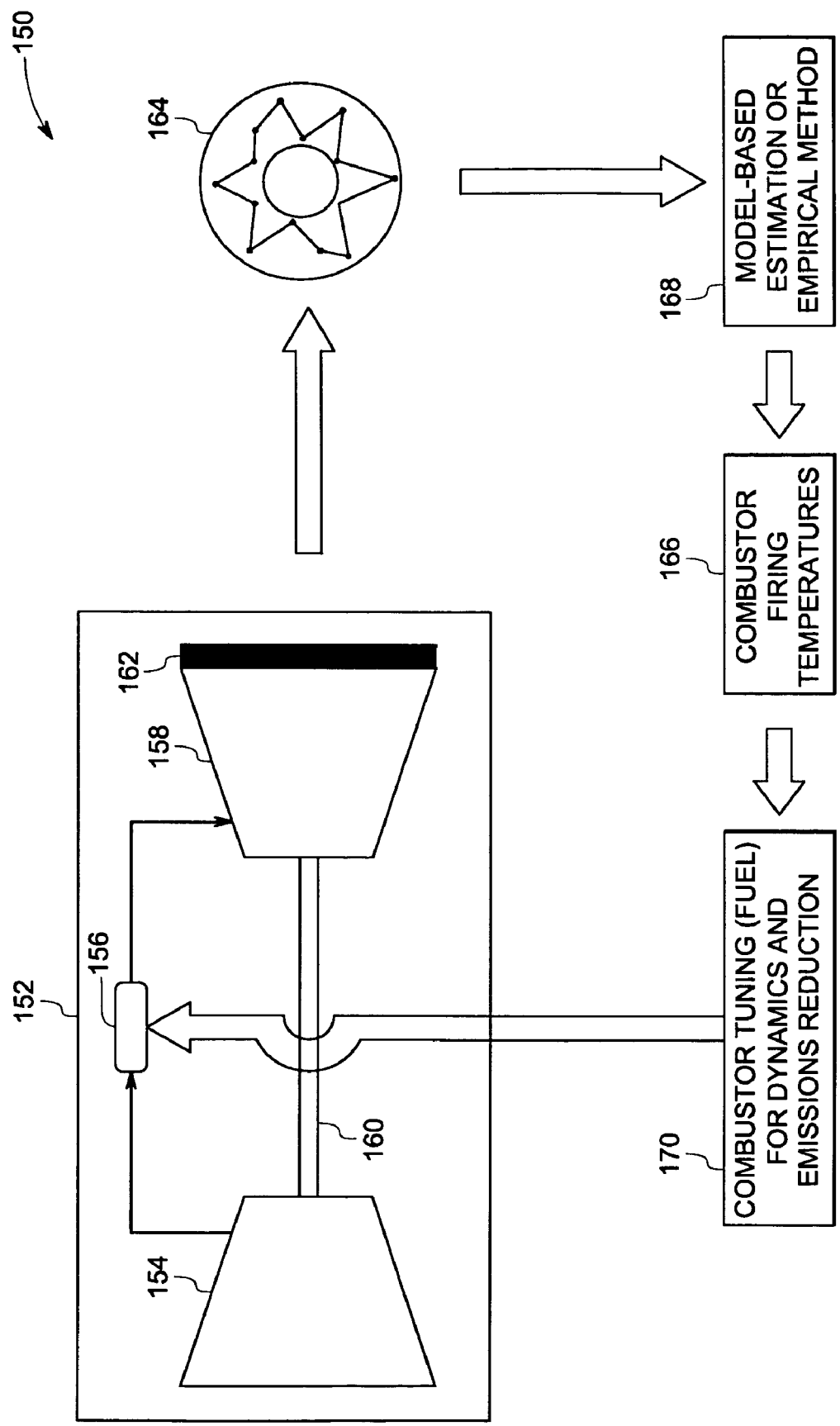
FIG. 11 is a diagrammatical representation of an application having the distributed fiber sensing system of FIG. 8 in accordance with an exemplary embodiment of the present technique.

The various aspects of the technique described above may be used for sensing multiple parameters such as, temperature, strain, pressure and fossil fuel gas in a variety of environments. In certain embodiments, the technique is employed for detecting parameters in a harsh environment such as those subjected to high temperatures. For example, the technique may be used for providing a thermal mapping in an exhaust system by measuring the temperature at multiple grating locations that are dispersed circumferentially about the exhaust system, or a combustor, or an output stage of a compressor of a jet engine. FIG. 11 illustrates an exemplary application 150 having the distributed fiber sensor system of FIG. 8.

Referring now to FIG. 11 the exemplary application 150 includes a gas turbine 152 having various components, such as a compressor 154, a multi-chamber combustor 156 and a turbine 158 disposed about a shaft 160. As illustrated, a distributed fiber sensor system 162 is coupled to the turbine 158 for providing a spatially dense exhaust temperature measurement 164 from the turbine 158. The temperature measurements 164 obtained by the distributed fiber sensor system 162 may be utilized for a substantially accurate control of the performance of the gas turbine 152. In the illustrated embodiment, the temperature measurements 164 may be utilized for determining combustor firing temperatures 166 through a model-based estimation technique or an empirical method 168. The model based estimation technique 168 utilizes an inverse of a physics based model that maps the combustor firing temperatures 166 to the exhaust temperatures 164. Alternatively, the empirical method 168 may utilize unload data of the turbine 158 to facilitate mapping of the exhaust temperatures 164 to the individual combustor chambers of the multi-chamber combustor 156. Advantageously, the spatially denser and more accurate exhaust temperature profile facilitated by the present exemplary embodiment increases the accuracy and the fidelity of the model based estimation and the empirical method.

The estimated combustor firing temperatures 166 may be utilized for adjusting fuel distribution tuning 170 to ensure that all chambers of the multi-chamber combustor 156 are firing uniformly and have dynamic pressures and emissions that are within pre-determined thresholds. Advantageously, the technique provides a substantial reduction in combustion chamber-to-chamber variation for emissions and firing temperatures 166.

Figure 12:
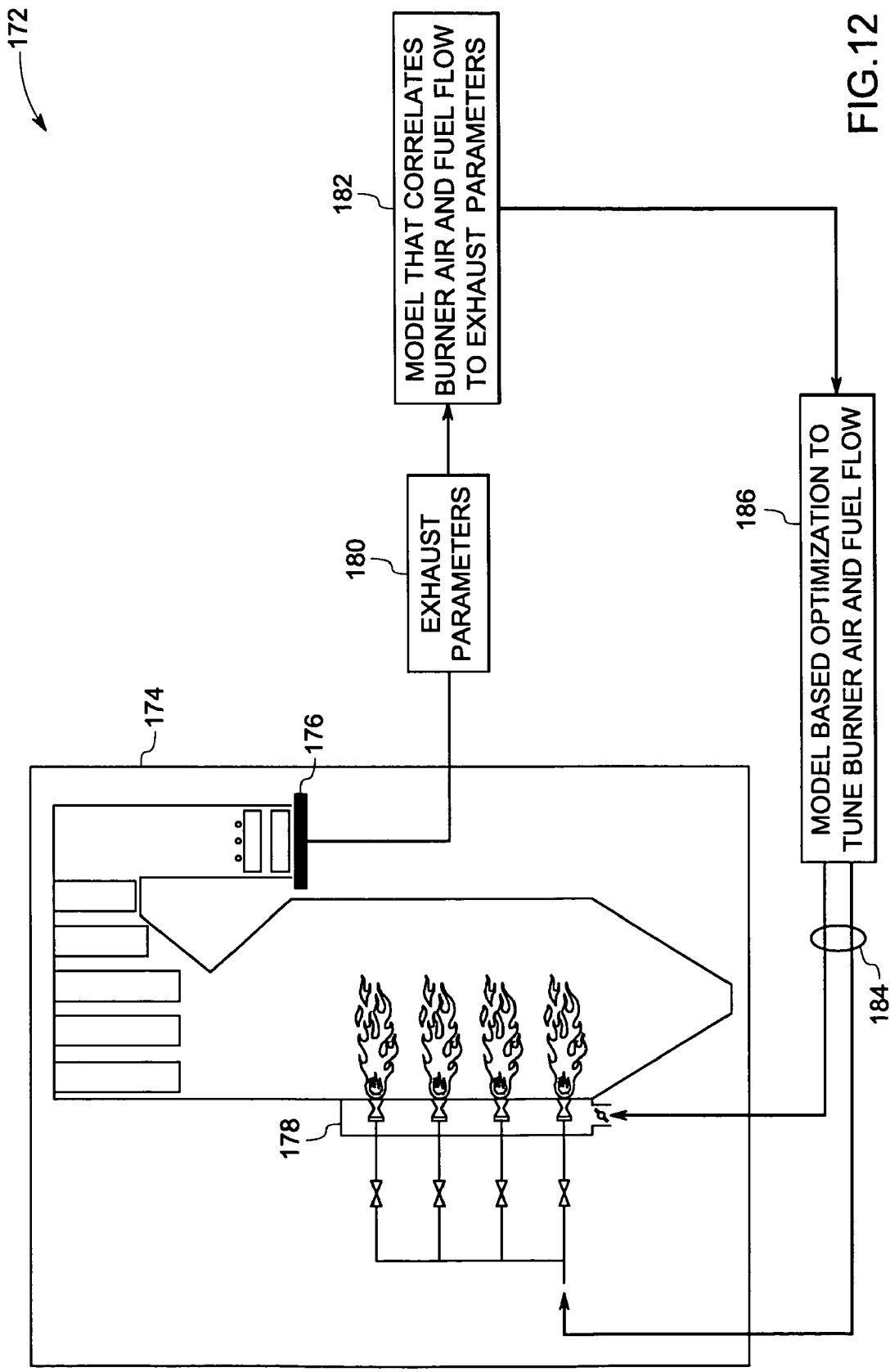
FIG. 12 is a diagrammatical representation of another application having the distributed fiber sensing system of FIG. 8 in accordance with an exemplary embodiment of the present technique.

FIG. 12 illustrates another exemplary application 172 having the distributed fiber sensor system of FIG. 8. As illustrated, the application 172 includes a coal fired boiler 174 for providing steam to steam turbines for power generation. The coal fired boiler 174 includes a distributed fiber sensor system 176 for measuring parameters such as temperatures, exhaust gases and so forth. In this embodiment, the measurement of parameters via the distributed fiber sensor system 176 may be employed to model relationship between inputs such as air and fuel flows to a burner 178 of the coal fired boiler 174 and exhaust parameters 180 from the boiler 174. Further, a model 182 may be employed to correlate the burner air and fuel flow to the exhaust parameter measurements 180 and to tune the air and fuel flows 184 via a model based optimization method 186. Advantageously, the exemplary sensor can provide more accurate and dense temperature profiles, CO and $O_2$ measurements in the exit plane of the boiler 174. Thus, air and fuel flows 184 may be adjusted to reduce exit temperatures, gas emissions such as CO while meeting desired output requirements.

Similarly, the technique may be used for mapping a temperature distribution in components such as gas turbines, steam turbines, distillation columns and so forth. The fiber optic sensing device as described above may be employed to estimate multiple parameters in an aircraft engine such as, a compressor blade tip clearance, compressor exit temperature, combustor temperature and for detecting exhaust tail pipe fire. For example, in detecting an exhaust tail pipe fire, the exemplary sensor described above can differentiate between abnormally high temperatures from normal elevated temperatures in locations that are not observable by the crew but are accessible by the sensor. Further, the fiber optic sensing device may be also employed for monitoring downhole sensing in an oil and gas drilling rig. The fiber optic sensing device may be employed in various other applications such as a narrow band reflector, a broadband mirror, a wavelength division multiplexing (WDM) filter, a differential photonic sensor and so forth.

Advantageously, in accordance with embodiments of the present technique, mapping temperature and fossil fuel gas species helps improve turbine and engine power production efficiency, thereby saving energy. For example, the exemplary periodic and aperiodic sapphire fiber-grating sensor array will simultaneously distinguish the temperature and gas by monitoring cladding modes wavelength shifts. The need for temperature sensing in industrial sensing and control applications has to simultaneously measure emissions (NOX, CO, O2, H2, etc.) of coal-fired boilers, gas turbines or steam turbine. The combined sensing helps optimize the turbine energy usage efficiency. The speed, accuracy and the spatial resolution of available extractive (offline) or non-extractive (online) gas sensing systems available today are limited. There is a need to improve speed of response, accuracy, and spatial resolution of such sensing systems so as to enable for instance better and possibly active closed loop emissions control for power generation equipment. For that matter, any control/optimization application that needs accurate and/or spatially denser gas sensing is a good candidate application for the multi-parameter sensors described herein.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method of detecting a plurality of parameters in an environment, comprising:
providing a source of light to a fiber optic sensor cable comprising a plurality of grating elements having a refractive index $n_a$ or a refractive index $n_b$, arranged in a quasiperiodic sequence, wherein the quasiperiodic sequence is defined by the equation $S_j=\{S_{j-1},S_{j-2}\}$ for j values greater than two, wherein $S_1=n_a$ and $S_2=n_an_b$; and
detecting light emitted from the fiber optic sensor cable.

2. The method of claim 1, further comprising determining a first diffraction peak corresponding to a first wavelength of the detected light and determining a second diffraction peak corresponding to a second wavelength of the detected light different from the first wavelength of light.

3. The method of claim 2, further comprising simultaneously measuring at least two different parameters corresponding to changes in the environment based on the first and second diffraction peaks.

4. The method of claim 3, wherein the measuring comprises detecting a temperature in the environment.

5. The method of claim 3, wherein the measuring comprises detecting a strain, or a stress, or a pressure, or any combination thereof in the environment.

6. The method of claim 1, further comprising providing a thermal mapping in an exhaust system of a gas turbine, or a steam turbine, or a coal fired boiler, or a combustor, or a compressor of a jet engine.

7. The method of claim 1, further comprising detecting at least one parameter in a gas turbine, or a steam turbine, or a coal fired boiler.

8. A method, comprising:
providing a source of light to a fiber optic sensor cable comprising a plurality of grating elements having a refractive index $n_a$ or a refractive index $n_b$, arranged in a quasiperiodic sequence, wherein the quasiperiodic sequence is defined by the equation $S_j=\{S_{j-1},S_{j-2}\}$ for j values greater than two, wherein $S_1=n_a$ and $S_2=n_an_b$;
reflecting a first wavelength of light via a first pair of grating elements such that waves of the first wavelength of light are in phase with one another;
reflecting a second wavelength of light via a second pair of grating elements such that waves of the second wavelength of light are in phase with one another; and
reflecting the first wavelength of light via a third pair of grating elements, wherein at least one grating element of the second pair of grating elements is located between at least one grating element of the first pair of grating elements and at least one grating element of the third pair of grating elements such that waves of the first wavelength of light are in phase with one another.

9. The method of claim 8, comprising reflecting a third wavelength of light via the third pair of grating elements in response to an environmental condition.

10. The method of claim 3, the presence of a pre-selected gas.

11. The method of claim 3, wherein the measuring comprises detecting mechanical stresses.

12. A method of fabricating a fiber optic sensing device, comprising:
providing a core having a first index of refraction;
providing a first pair of grating elements configured to reflect a first wavelength of light in phase, wherein the distance between adjacent grating elements of the first pair is at a first distance;
providing a second pair of grating elements configured to reflect a second wavelength of light in phase, wherein the distance between adjacent grating elements of the second pair is at a second distance;
providing a third pair of grating elements configured to reflect the first wavelength of light in phase, wherein at least one grating element of the second pair of grating elements is located between at least one grating element of the first pair and at least one grating element of the third pair,
wherein the first, second, and third pairs of grating elements have a refractive index $n_a$ or a refractive index $n_b$ and are arranged in a quasiperiodic sequence wherein the quasiperiodic sequence is defined by the equation $S_j=\{S_{j-1},S_{j-2}\}$ for j values greater than two, wherein $S_1=n_a$ and $S_2=n_an_b$; and
disposing a cladding circumferentially about the core.

13. The method of claim 12, further comprising providing a light source for illuminating the core for generating diffraction peaks representative of sensed parameters via the first, second and third pair of grating elements.

14. The method of claim 12, further comprising coupling a detector system to the fiber optic sensing device for determining the sensed parameters based upon the diffraction peaks generated from the fiber optic sensing device.

15. The method of claim 12, comprising providing the first, second and third pair of grating elements disposed in a fused silica fiber.

16. The method of claim 12, comprising providing the first, second and third pair of grating elements disposed in a sapphire fiber.

17. The method of claim 12, comprising providing the first, second and third pair of grating elements though a ultraviolet light exposure laser inscribing technique.

18. The method of claim 12, comprising providing the grating elements such that alternating distances between adjacent gratings along a longitudinal axis of the core between the first distance and the second distance are present.

19. The method of claim 12 wherein providing the first, second, and third pairs of grating elements comprises;

mechanically altering the core to form altered portions within the core.

20. The method of claim 19, wherein mechanically altering comprises altering a diameter of the fiber optic sensor cable though a diamond saw cutting technique.

* * * * *

UNITED STATES PATENT AND TRADEMARK OFFICE
CERTIFICATE OF CORRECTION

PATENT NO.         : 7,492,980 B2
APPLICATION NO.    : 12/107340
DATED              : February 17, 2009
INVENTOR(S)        : McCarthy et al.

It is certified that error appears in the above-identified patent and that said Letters Patent is hereby corrected as shown below:

In Column 12, Line 26, in Claim 10, after "Claim 3," insert -- wherein the measuring comprises detecting --.

In Column 13, Line 5, in Claim 17, delete "though" and insert -- through --, therefor.

In Column 14, Line 8, in Claim 20, delete "though" and insert -- through --, therefor.

Signed and Sealed this

Fourteenth Day of July, 2009

JOHN DOLL
*Acting Director of the United States Patent and Trademark Office*